United States Patent [19]

Pontius et al.

[11] Patent Number: 5,386,731
[45] Date of Patent: Feb. 7, 1995

[54] METHOD AND APPARATUS FOR MEASURING THE TENSILE STRENGTH OF POWDERS

[75] Inventors: Duane H. Pontius, Gardendale; Todd R. Snyder, Birmingham, both of Ala.

[73] Assignee: Southern Research Institute, Birmingham, Ala.

[21] Appl. No.: 149,130

[22] Filed: Nov. 5, 1993

Related U.S. Application Data

[63] Continuation of Ser. No. 832,681, Feb. 7, 1992, abandoned, which is a continuation of Ser. No. 579,860, Sep. 7, 1990, abandoned.

[51] Int. Cl.$^6$ .............................. G01N 3/08
[52] U.S. Cl. ..................................... 73/834
[58] Field of Search .............. 73/760, 866, 834; 324/663-695

[56] References Cited

U.S. PATENT DOCUMENTS

| | | | |
|---|---|---|---|
| 4,051,431 | 9/1977 | Wurster | 324/663 |
| 4,238,030 | 12/1980 | Maylandt | 361/212 |
| 4,540,936 | 9/1985 | Walsh | 324/668 |
| 4,928,065 | 5/1990 | Lane et al. | 324/439 |

OTHER PUBLICATIONS

"Flow Properties of Bulk Solids", American Society for Testing Materials Proceedings, vol. 60, pp. 1168-1190 (1960) Jenike et al.

Pohl, "A Novel Ring Shear Device for the Purpose of Classification of Fine Powders" presented at 17th Annual Conference of the Fine Particle Society, (1986).

Penney et al., "Contact Potentials and the Adhesion of Dust", Transactions of the American Institute of Electrical Engineers I, vol. 81:200 (1962): Communications and Electronics, No. 61 (Jul. 1962).

Oglesby et al., "Electrostatic Precipitation", Marcel Dekker, Inc., New York, 1978 pp. 106-107.

Tassicker, "Aspects of Forces on Charged Particles and Electrostatic Precipitators" EPRI Report Ph.D. Dissertation, University of New South Wales, 1972.

Durham, et al., "Low-Resistivity Related ESP Performance Problems in Dry Scrubbing Applications," Journal of the Air and Waste Management Association 40(1):112 (1990).

*Primary Examiner*—Robert Raevis
*Attorney, Agent, or Firm*—Needle & Rosenberg

[57] ABSTRACT

A method and apparatus for measuring the tensile strength of aggregate material comprising a device in which a layer of dust is applied to a metal electrode, and an electric field is applied in such a way as to induce a charge (negative or positive) on the outer surface of the dust layer. The electric field is then increased until particles break away from the upper surface as a result of the electrostatic force acting on the induced charge. From the balance of forces between the electrostatic (which is easily calculated from the configuration and applied voltage) and the cohesive attraction between the particles, the tensile force of the dust layer is determined. The breakaway point may be observed directly, or it may be detected by a photoelectric device designed to respond to light scattered by the particles as they are lofted from the surface. Alternatively, the breakaway point may be detected by sensing an electric current concomitant with the ejection of surface charge residing in the lofted particles.

4 Claims, 3 Drawing Sheets

METHOD AND APPARATUS FOR MEASURING THE TENSILE STRENGTH OF POWDERS

The U.S. government has rights in this invention under EPA Cooperative Agreement CR814915-01.

This application is a continuation of application Ser. No. 07/832,681, filed Feb. 7, 1992, now abandoned, which is a continuation of application Ser. No. 07/579,860, filed Sep. 7, 1990, now abandoned.

BACKGROUND OF THE INVENTION

This invention relates generally to the field of powder technology and, more particularly, to a method and apparatus for measuring the cohesive forces in aggregates of particulate matter.

The tensile, or cohesive, strength of dust aggregates affects the reentrainment of dust in electrostatic precipitators and the removal of dust cakes from fabric filters, but it is a very difficult quantity to measure directly. Conventional methods are based on the application of forces on particulate samples by mechanical means. Such techniques for measuring tensile strength can be ineffective or inaccurate because the forces holding particles together are very small. The problems that arise in using a mechanical approach, include friction and inertia in the apparatus, and the difficulties of attaching the apparatus to a sample. The problem is also complicated by the heterogeneity of inter-particle forces that arises from the range of particle sizes in most applications of interest.

The cohesive forces among particles are often described in terms of measured values of reactions to shear stresses. Several methods have been used, ranging from the simple split-ring Jenike cell to the complex ring shear device. The advantages of the relatively simple design of the Jenike cell are offset by lengthy test procedures and a strong dependence on preparation of the sample. In contrast, characterizations of cohesive forces performed with ring shear devices are quicker and less operator-dependent. However, these devices are quite expensive. Methods and equipment are also presently available for the direct measurement of the tensile strength of powders. The procedures and equipment used in these methods are also relatively complex, due to the difficulties inherent in mechanically applying and measuring tensile stresses. Thus, the instant invention provides a novel approach to the measurement of a quantity that is important to various aspects of flue gas clean up and fine powder handling.

SUMMARY OF THE INVENTION

The above disadvantages of the prior art for measuring the tensile strength of aggregates are overcome by the present invention which involves the use of an electrostatic force to bring about the separation of particles to provide a sensitive measurement of the cohesive forces between them. The invention is based on exerting a distributed mechanical force on a layer of dust by application of an electric field. The field induces a charge on the exposed surface of the layer and then it acts on that charge to pull on the surface particles against the forces of cohesion. The onset of the effluence of dust from the surface is then observed. The point at which tensile failure occurs can be identified fairly repeatedly in spite of the uncertainties that arise from the variety of particle sizes. From the balance of forces between the electrostatic (which is calculated from the configuration and applied voltage) and the cohesive attraction between the particles, the tensile force of the dust layer is determined.

The present invention is particularly useful in the technology of electrostatic precipitation and the theory of reentrainment of dust (i.e., the reintroduction of the dust accumulated on the collection plates in electrostatic precipitators as the dust is transferred to the dust removal system). The cohesive forces that tend to hold the dust layer together are important because, without them, the dust would simply fall off the plates whenever the precipitator is turned off. In some instances, cohesion can be the dominant consideration in determining whether or not reentrainment will be an important problem. Measurement of the tensile strength of a specific dust can be achieved by the present invention and thus, whether or not electrical reentrainment will be inhibited.

The method and apparatus of the present invention involves a pair of spaced, parallel plate electrodes, with a dust layer being placed upon the bottom electrode. Voltage is gradually applied between the electrodes until the particles are lofted from the electrode surface, with the onset of particle ejection from the dust layer being specifically the desired measurement. A laser beam illuminates the space between the electrodes so that the observation may be enhanced. A video camera observes the laser light scattered by the particles as they pass through the beam.

BRIEF DESCRIPTION OF THE OF DRAWINGS

DETAILED DESCRIPTION OF THE ILLUSTRATIVE EMBODIMENT

Figure 1:
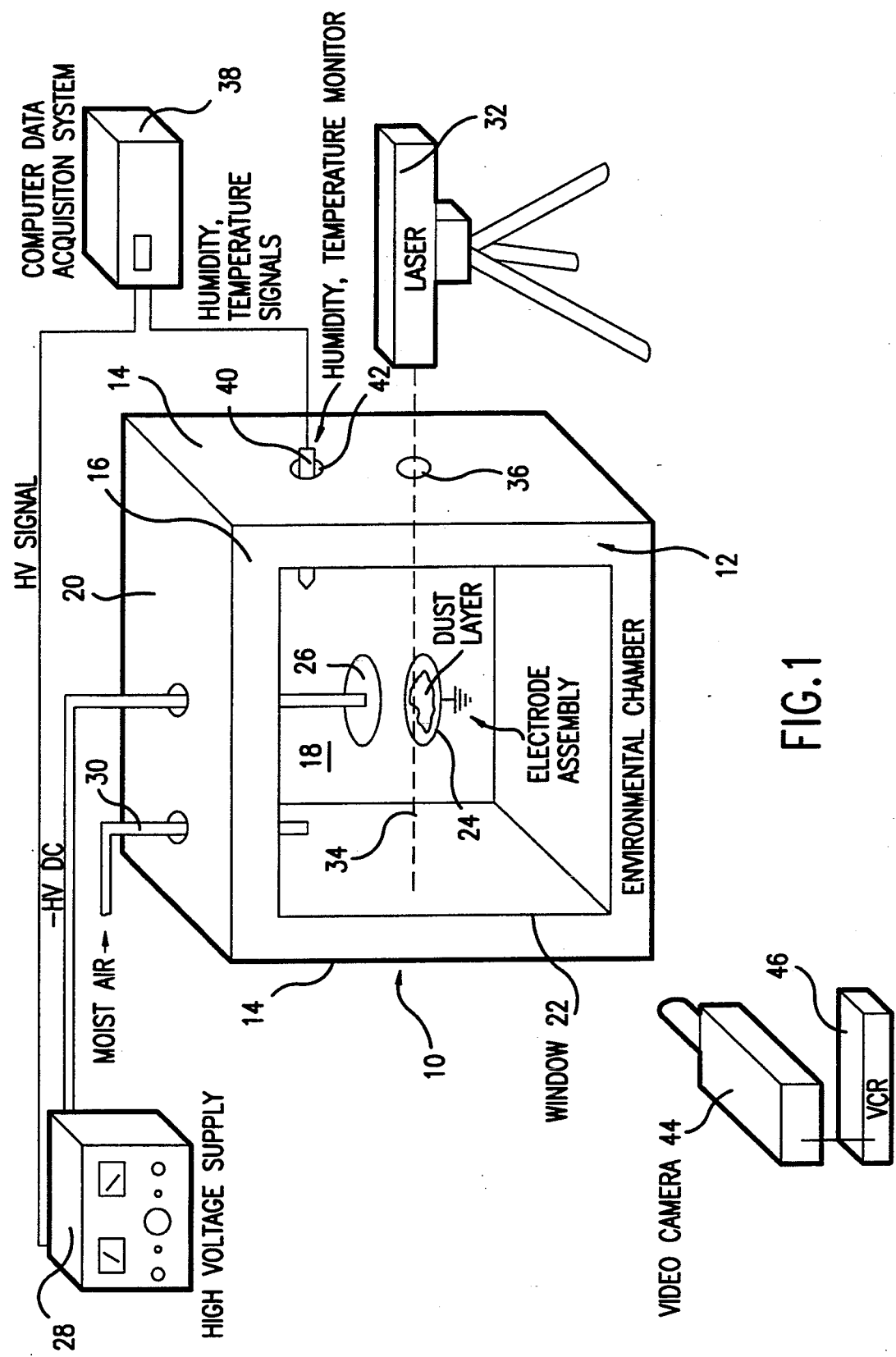
FIG. 1 is a schematic view of the apparatus utilized in measuring the tensile strength of powders.
Figure 2:
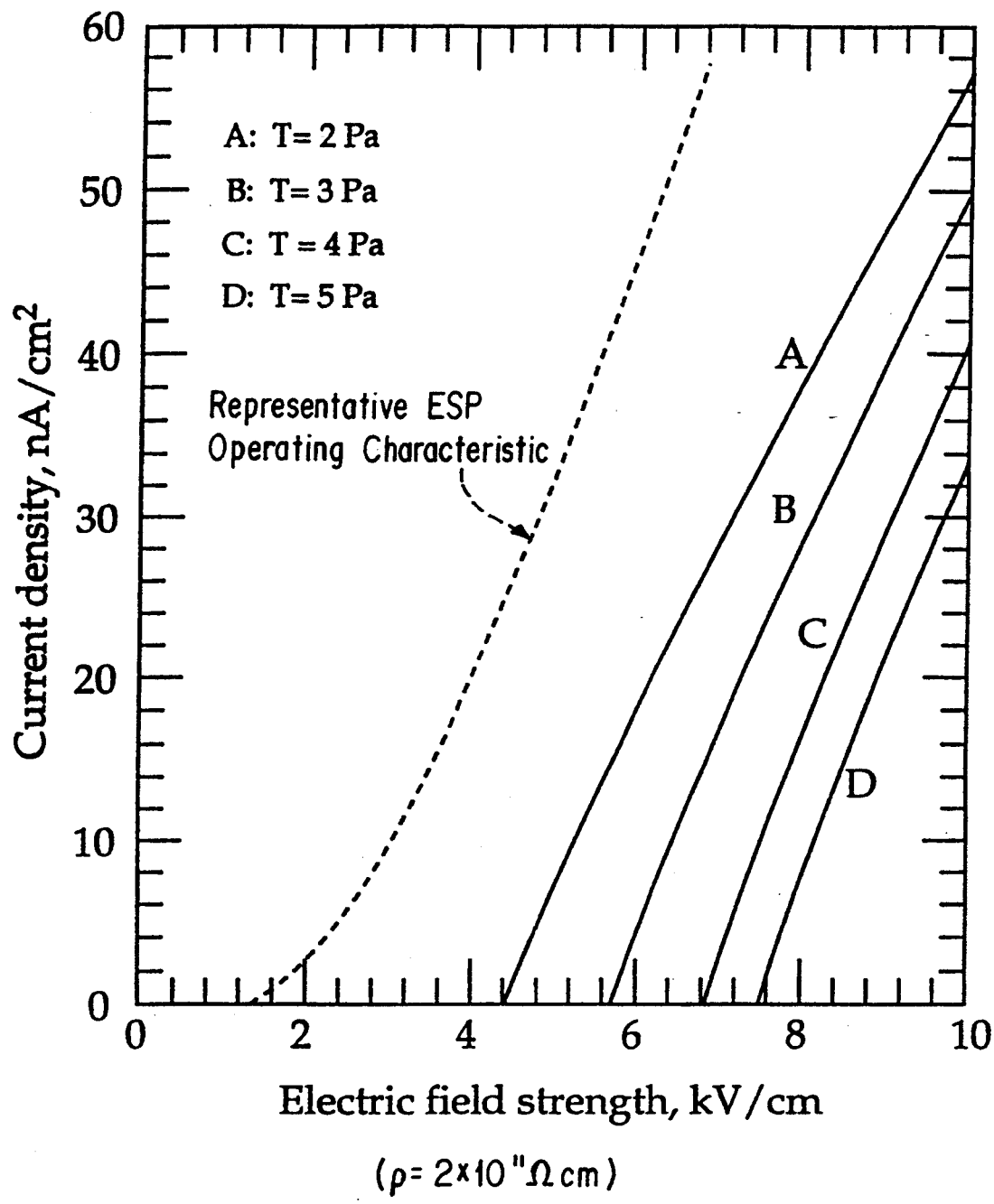
FIG. 2 is a graph depicting reentrainment boundaries for various values of tensile strength. The dashed curve is a representative operating characteristic for an ESP and $\rho = 2 \times 10^{11}$ $\Omega$cm.
Figure 3:
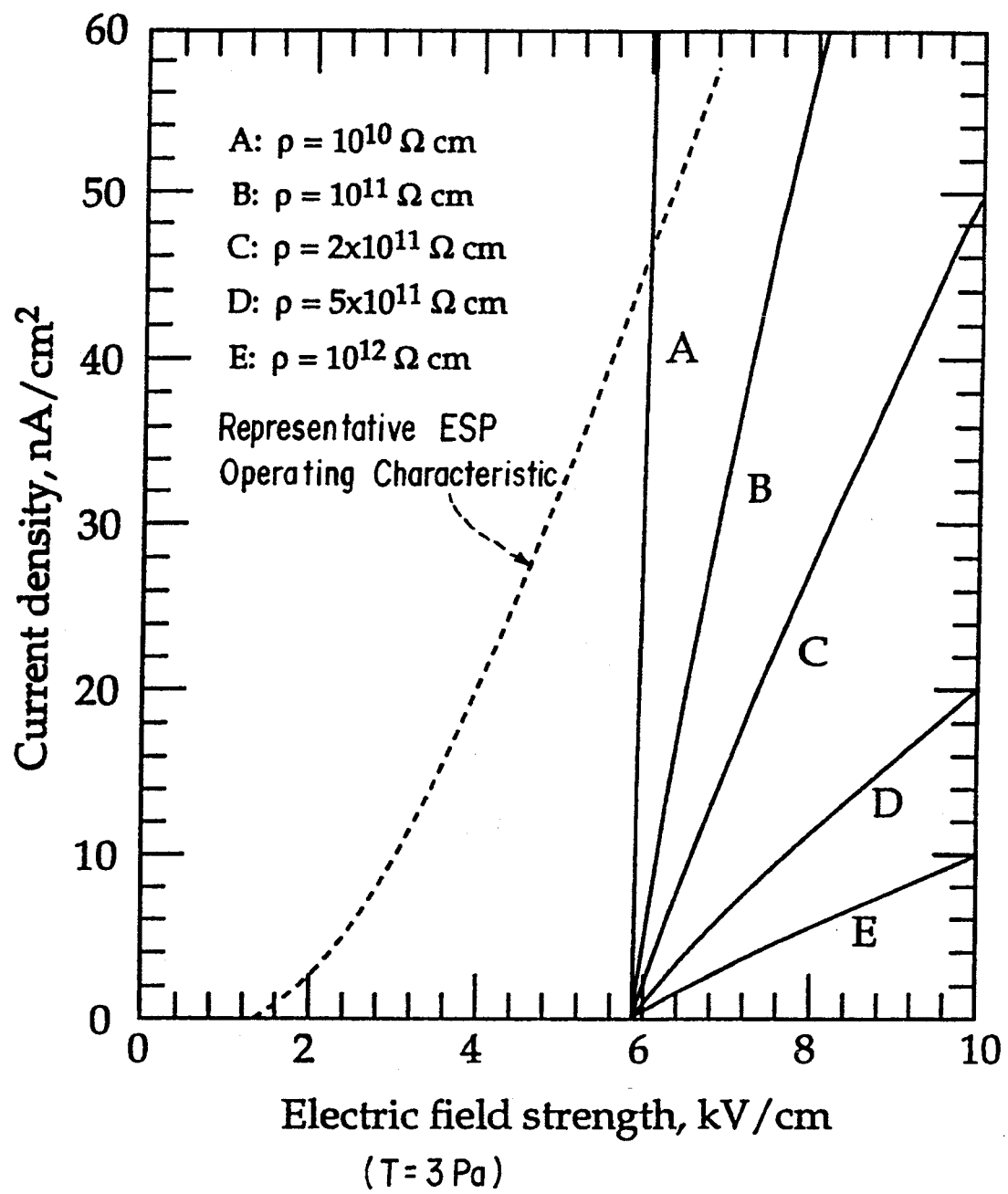
FIG. 3 is a graph depicting reentrainment boundaries for various values of electrical resistivity. The dashed curve is a representative operating characteristic for an ESP and T=3 Pa.

Modern requirements for emissions control include standards for abatement of both $SO_2$ and fly ash. These two pollutants pose different kinds of control problems, and consequently various combinations of gaseous and particulate control devices have been tried. One such system, designated E-SOx by its developers, comprises a method for removing sulfur oxides with an aqueous spray of an alkaline material upstream of an electrostatic precipitator. The process has been studied to determine the effectiveness of $SO_2$ removal and the effect of the resulting changes in the gas stream on the operation of the precipitator. As a result of these studies, there are indications that anomalous, size-dependent reentrainment of particles causes severe degradation of the collection efficiency of precipitators used in this kind of application. This problem has been the subject of a combined theoretical and experimental program, which has led to a modification of the conventional theory of electrostatic reentrainment by the inclusion of tensile (cohesive) forces between particles. The presence of relatively large numbers of fine particles in the reentrained material is explained by a decrepitation of agglomerates as a result of polarization and electrical stress in the electrostatic field.

The dust layer that accumulates on the collecting surfaces of an electrostatic precipitator is held in place by both electrodynamic and cohesive forces. The electrodynamic effects are reasonably well understood; however, the connection with the cohesivity of the dust is usually treated qualitatively. In the following discussion, it will be assumed that the polarity of the corona discharge is negative.

Conduction in an electrostatic precipitator occurs by different mechanisms in the gas and in the dust layer, but continuity of current density ties the two together at the boundary. Negative ions, primarily $O^-$ and $O_2^-$ carry the corona current through the gas, and positive ions, such as $Na^+$, are responsible for the current in the dust layer. The positive and negative ions meet and exchange charge at the outer surface of the dust layer. Thus, in the steady state, the current density approaching the surface of the dust layer must be the same as the current density in the layer. As a general rule, there is a surface charge layer on the boundary to account for the differences in electric field strength in the two different media. The magnitude of the surface charge density depends upon several parameters, including the electrical resistivity and the relative dielectric constant of the dust layer, as well as the electrode configuration and the applied potential. It is possible for the surface charge to be of either positive or negative polarity.

If the charge layer is negative, corresponding to the polarity of the corona discharge, the electrical force will tend to push the dust layer toward the collecting surface. This kind of behavior is usually associated with a dust of relatively high resistivity. Conversely, if the charge layer is positive, the electric fields will tend to pull it away from the surface. This action can result in serious reentrainment of collected dust.

In addition to the electrostatic effects, cohesive effects can be included in the balance of forces on a dust layer, and useful, quantitative methods for applying this theory will be described.

Theoretical Development

In the conventional theory, the criterion marking the threshold of electrostatic reentrainment was taken to be the point at which the surface charge density on the dust layer changes over from the same to the opposite of the polarity of the corona discharge electrode. This inversion occurs if the resistivity of the dust becomes small enough that the induced charge passing through the dust layer from the plate is greater than the charge deposited by the ionic current of the corona discharge. This theory is incomplete, however, because it neglects the cohesive forces between the particles.

The theoretical basis for this study concerns the behavior of a layer of dust on a grounded, electrically conductive plate. In the first approximation the dust layer will be treated on the macroscopic scale as a homogeneous solid that has electrical resistivity $\rho$, relative dielectric constant k, and tensile strength T. An electrode is placed at a distance from the surface of the dust layer, and connected to a source of electrical potential. The shape and potential of this electrode may or may not produce a corona discharge. In the most general case, at a localized region of the dust layer there will be a current density j, and electric field of magnitude $E_d$ in the dust. In the space immediately outside the dust layer the electric field strength is $E_s$. The equations will be based on local conditions on a small region of the surface, and edge effects will be neglected (that is, only normal components of the forces and fields will be considered.)

The electrical conditions applied will determine the surface charge density $\delta$ on the dust layer. The source of the charge may be from the corona discharge or from conduction through the layer, depending upon the current density and the resistivity of the dust. The boundary condition at the surface determines the relationship between $E_s$, $E_d$, and $\sigma$. In general, the change in the electrical displacement, $k\epsilon_0 E$, across a boundary is equal to the surface charge density. Thus, in MKS units, $$\sigma = \epsilon_0(E_s - kE_d) \tag{1}$$

in which $\epsilon_0$ is the permittivity of free space, $8.85 \times 10^{-12}$ F/m, and it has been assumed that the relative dielectric constant of the gas is 1. Since the dust layer has a known value of resistivity $\rho$, and current density j is a measurable quantity, the electric field strength in the dust layer can be determined simply as the product of j and $\rho$.

The force per unit area p, on the surface of the dust layer is the sum of the electrostatic pressure and the tensile force. This sum represents the stress across the boundary layer. The electrostatic pressure (force per unit area) is the product of the surface charge density and the combined effect of the electric fields $E_s$ and $E_d$:

$$p = (E_s + E_d)\sigma - T \tag{2}$$

The equation is written in scalar form because all vectors of interest are approximately normal to the surface. The direction of positive p is outward normal to the surface of the dust layer. Combining equations 1 and 2, the balance of forces may be expressed in the form $$p = \epsilon_0(E_s + E_d)(E_s - kE_d) - T = \epsilon_0[E_s^2 - kE_d^2 - (k-1)E_s E_d] - T \tag{3}$$

The form of this equation suggests a way to measure T. If the electrodes are designed to avoid corona discharge, then j will remain zero, and hence, $E_d$ will be zero. At the threshold for effusion of dust from the surface, p passes through zero. The remaining terms of the equation under these conditions give T as a simple function of the electric field at the point of effusion $E_s(0)$:

$$T = \epsilon_0[E_s(0)]^2 \tag{4}$$

Therefore, the tensile strength of a specific dust can be determined experimentally and inserted into equation 3. Since k, $E_s$ and $E_d$ can be measured or calculated, the actual holding force (or expulsive force) can be calculated for any given operating condition. In the following paragraphs, the effects of variations in cohesivity and electrical resistivity on this force will be discussed.

The operating point of an electrostatic precipitator can be plotted in terms of the current density and the electric field strength at the boundary between the gas and the dust layer. At each point on the graph, the value of p can be calculated by making the substitution $E_d = j\rho$. Since p includes both electrodynamic and cohesive forces, a positive value of p indicates reentrainment, and a negative value means that- the dust will remain on the surface. The locus of points for which p=0 defines the boundary between these conditions, and a graph of this locus is a useful representation for examining the effects of resistivity and tensile strength on reentrainment of a dust layer in an electrostatic precipitator.

Equation 3 is quadratic in the variable $E_d$. If the product $j\rho$ is substituted for $E_d$ and the equation is solved for j, the result is as follows:

$$j = \frac{1}{2k\rho}\left[(1-k)E_s + \sqrt{(k+1)^2E_s^2 - \frac{4kT}{\epsilon_0}}\right] \quad (5)$$

This function is plotted in FIG. 2 for four different values of T, along with a representative operating curve for an ESP. For each of the four curves based on equation 5, the area to the left is favorable, and the area to the right indicates conditions for electrical reentrainment. It is obvious in a qualitative sense that increasing the tensile strength of the dust layer should inhibit reentrainment, and this graph shows the effect quantitatively.

FIG. 3 is a similar graph, except that the tensile strength of the dust is held constant and various values of electrical resistivity are represented. Again, previous knowledge about reentrainment is supported and augmented. The curves have a common intercept on the ordinate, which indicates that resistivity has no effect on the surface charge when the current density is zero. When no current is present the electric field in the dust layer must be zero, and the surface charge density is independent of the resistivity. If there is a current passing through the dust, it is connected to the electric field in the dust layer by the proportionality constant $\rho$. Therefore, as $\rho$ is increased, both the surface charge density and the field are affected. The effect shown in FIG. 3 is that an increase in resistivity expands the space in which favorable operating conditions (from the standpoint of reentrainment) can be achieved. The total space available for good overall operating conditions may or may not increase, since a higher resistivity results in a reduced limit on the current density before the onset of back corona.

The problem of reentrainment is somewhat more complex when viewed on the microscopic scale, because the dust layer is typically a very heterogeneous material. Reentrainment on this scale can be explained in terms of forces similar to those expressed in the above equation, but operating on individual particles and small aggregates. The logic of this approach supports the proposition that, when clusters of particles are reentrained, they are first polarized and then subjected to tensile stresses that are comparable to those that led to their reentrainment. Observations in the laboratory have confirmed that these forces are sufficient to break up the clusters, or agglomerates, very quickly as they move away from the dust layer.

MEASUREMENT OF TENSILE STRENGTH (T)

As seen in FIG. 1, the apparatus for measuring the tensile strength of the dust is referred to generally by the numeral 10 an comprises an environmental chamber 12 having sides 14, front 16, back 18 and top 20. A viewing window 22 is provided through front 16. The chamber 12 is a standard Blue M laboratory oven modified to provide stable temperature and humidity levels. A pair of parallel, spaced plate electrodes 24, 26 are suspended within the chamber 12 with lower electrode 24 being grounded and upper electrode 26 being connected through top 20 to a high voltage supply 28. Alternatively, the upper and lower electrodes are connected so that the lower electrode remains at a voltage opposite in polarity with respect to the upper electrode during operation. The electrode assembly is designed to provide parallel, flat surfaces without sharp edges. The two electrodes 24, 26 are essentially identical with the only differences being the electrical connections and physical support surfaces. The high voltage power supply 28 is a Hipotronics Model 850A which provides well-regulated negative polarity DC at levels up to 60 KV. Humidity levels in chamber 12 are generated through conduit 30 which extends into the chamber 12 through top 20 and is connected to a source of air (not shown) which is bubbled through a constant-temperature water bath.

A helium-neon laser 32 is positioned outside chamber 12 adjacent a side 14 so as to provide a beam 34 through transparent window 36 adjacent the top surface of lower electrode 24. A computer data acquisition system 38 is connected to the voltage source 28 and to a probe 40 that is inserted through opening 42 in side 14; the probe 40 monitors the humidity and temperature within chamber 12. The computer acquisition system 38 monitors the voltage applied to the upper electrode 26 and also records and displays relative time, temperature and relative humidity. Finally, a video camera 44 connected to a VCR 46 is positioned in front of window 22 so as to record the results. The resultant video recording made during measurements is manually synchronized to the relative time recorded by the computer data acquisition system 38.

The parallel plate electrodes 24, 26 are well suited to satisfy the conditions imposed by equation 4. This arrangement of electrodes provides a uniform electric field that is easy to calculate, and it allows comparatively high electric field strength to be applied without a corona discharge. In the experiments of the present invention, the electrodes 24, 26 were separated by approximately 5 cm. Since the area and thickness of the dust layer do not enter into the theory (unless the thickness is a significant fraction of the spacing between the plates), a region near the center of the electrode is covered with a smooth layer of dust so that the variation of field strength across the layer would be minimized. Because temperature and humidity levels can affect the cohesive forces acting between the particles in the dust layer, the temperature and humidity levels, as monitored by probe 40, were controlled within chamber 12.

A voltage was applied between the electrodes 24, 26, increasing gradually until particles were lofted from the surface. The onset of particle ejection was taken to be the point at which equation 4 was satisfied. In terms of experimental variables, T is calculated from:

$$T = \epsilon_0 V_e^2 / h^2 \quad (6)$$

In this expression, $V_e$ is the applied potential at the onset of effusion, and h is the separation between electrodes 24, 26.

There is some range of uncertainty as to the onset. On the microscopic scale, the phenomenon can be looked upon as the lifting of individual particles from the surface. The electrostatic and cohesive forces differ among the particles because of variations in their sizes. Of course, these variations also affect the nature of the tensile strength, since it is a bulk effect, and the breakage of weak bonds increases the stress on the stronger bonds, leading finally to fracture. Thus the heterogeneous microstructure of dust aggregates in general affects both the cohesive forces on the microscopic scale and the tensile strength on the macroscopic scale. The observation of particle movement into the open space between electrodes 24, 26 was enhanced by illuminating the region with laser beam 34 from laser 32 which was mounted so that the beam 34 was parallel to the surface of the dust layer and slightly above it. A video camera 44 and VCR 46 were used to observe laser light scattered by the particles as they passed through the beam 34.

In observing the dust layer as the applied voltage is increased, a small number of individual particles (or possibly small clusters) flew off of the surface at random intervals. The behavior then changed fairly sharply to an appearance of clouds of particles. This latter transition is interpreted as the appropriate point to identify with tensile breakdown. If the voltage is held constant at this level, the action of the particles diminishes almost to a stop, and a higher voltage is required to restart the effusion. Apparently, there is a depletion of particles within the range that is most susceptible to electrostatic removal from the surface, although most of the dust layer remains undisturbed. The electrostatic field induces a charge on the upper surface of the dust layer, so the internal field is zero, and hence no forces are exerted on particles below the surface. Of course, new particles are exposed to the surface and take on an induced charge after those on the surface above them are removed, but statistically, many of those newly exposed will be less susceptible to removal than those that have already been removed. Conversely, many of the more easily ejected particles may remain shielded from the surface by particles that are more difficult to pull off electrostatically.

Initial measurements were performed on a 1 mm thick, smooth layer of dust manually spread on the grounded electrode 24. (The dust used in these experiments was quicklime which had been electrostatically precipitated following slurry injection tests performed at a pilot-scale combustion facility.) The edges of the dust layer were located away from the edges of the plate 24. Repeated measurements were made at 69° C. and moisture levels of 14% water content by volume. At these conditions the initial effusion of clouds of dust particles was observed at a field strength of 8 KV/cm. Observation of the dust layer following the tests indicated that effusion of particles had roughened the ash layer. The tensile strength of the dust layer, calculated by application of equation 4 is 5.6 Nt/m$^2$.

An alternative, and possibly simpler approach, to the detection of particle ejection from the surface is to insert an electrometer in the wire that connects the lower electrode 24 to ground potential. Since the particles carry some charge with them as they travel from one electrode to the other, their motion constitutes an electrical current. Before the onset of effusion, there is no electrical current, so the onset of current is the required data point for measurement. The currents involved in such measurements would be relatively small, but not below the sensitivity of modern electrometers.

A further alternative of the present invention involves the placement of a photodetector in the environmental chamber 12 to detect the onset of scattered light generated by the passage of reentrained particles through the region of laser illumination. The signal from the photodetector would be incorporated directly into the computer data acquisition system 38 to allow very accurate correlation of the onset of reentrainment with the applied voltage. A suitable photodetector systems would probably negate the need for the video camera/recording system 44, 46.

Another embodiment of the existing system would be an automated method for increasing the applied voltage at a uniform, reproducible rate prior to the effluence of dust from the layer. (Presently, voltage is manually raised during the measurement procedure. Differences in the rate of voltage increase may influence the onset voltages measured for particle effluence.)

In an alternative embodiment of the present invention, the breakaway point may be detected by sensing an electrical current concomitant with the ejection of surface charge residing on the lofted particles.

It is to be understood that the forms of the invention described and illustrated herein are to be taken as preferred examples of the same, and that various changes in the arrangement and type of components may be made without departing from the spirit of the invention or the scope of the subjoined claims.

What we claim is:

1. A method for determining the tensile strength of a dust aggregate comprising the steps of:
    a) placing a sample of said dust aggregate on the lower of two spaced, parallel, horizontally disposed plate electrodes, wherein said plates and said sample are in a gaseous environment;
    b) creating an electric field between said two plate electrodes, wherein the magnitude of the field is below that which will produce a corona discharge;
    c) varying said electric field;
    d) detecting when effusion of particles from said sample begins;
    e) measuring and recording the value of said electric field when said effusion begins; and
    f) calculating said tensile strength using said measured value of electric field.

2. A method as claimed in claim 1, wherein said step of detecting effusion of particles comprises the step of optically sensing particles in the space between said electrodes.

3. A method as claimed in claim 1, wherein said step of detecting effusion of particles comprises the step of sensing an electrical current resulting from the ejection of surface charge residing on the lofted particles.

4. The method as claimed in claim 1, further comprising the step of measuring the humidity and temperature of said gaseous environment when said effusion begins.

* * * * *